(12) United States Patent
Chen et al.

(10) Patent No.: US 7,649,220 B2
(45) Date of Patent: Jan. 19, 2010

(54) PHOTODETECTOR HAVING DARK CURRENT CORRECTION

(75) Inventors: Farn Hin Chen, Perak (MY); Gim Eng Chew, Penang (MY); Boon Keat Tan, Penang (MY)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 393 days.

(21) Appl. No.: 11/693,518

(22) Filed: Mar. 29, 2007

(65) Prior Publication Data
US 2008/0239321 A1    Oct. 2, 2008

(51) Int. Cl.
*H01L 31/062*  (2006.01)
(52) U.S. Cl. ............... 257/293; 257/291; 257/292; 257/233
(58) Field of Classification Search ........... 257/291, 257/292, 293, 233
See application file for complete search history.

(56) References Cited

U.S. PATENT DOCUMENTS 7,285,768 B2 * 10/2007 Tan et al. ............. 250/226
7,435,943 B1 * 10/2008 Chen et al. ........... 250/226

* cited by examiner

*Primary Examiner*—Long Pham

(57) ABSTRACT

A photodetector and method for making the same is disclosed. The photodetector includes a substrate having first, second, and third photodiodes and first and second pigment filter layers. The first, second, and third photodiodes generate first, second, and third photodiode output signals, respectively, each photodiode output signal being indicative of a light intensity incident on that photodiode and a dark current that is independent of the light intensity. The first and second pigment filter layers overlie the first and second photodiodes while a layer having both the first and second pigment filter layers overlie the third photodiode. An output circuit combines the first and third photodiode output signals to provide a first corrected output signal and combines the second and third photodiode output signals to provide a second corrected output signal.

7 Claims, 3 Drawing Sheets

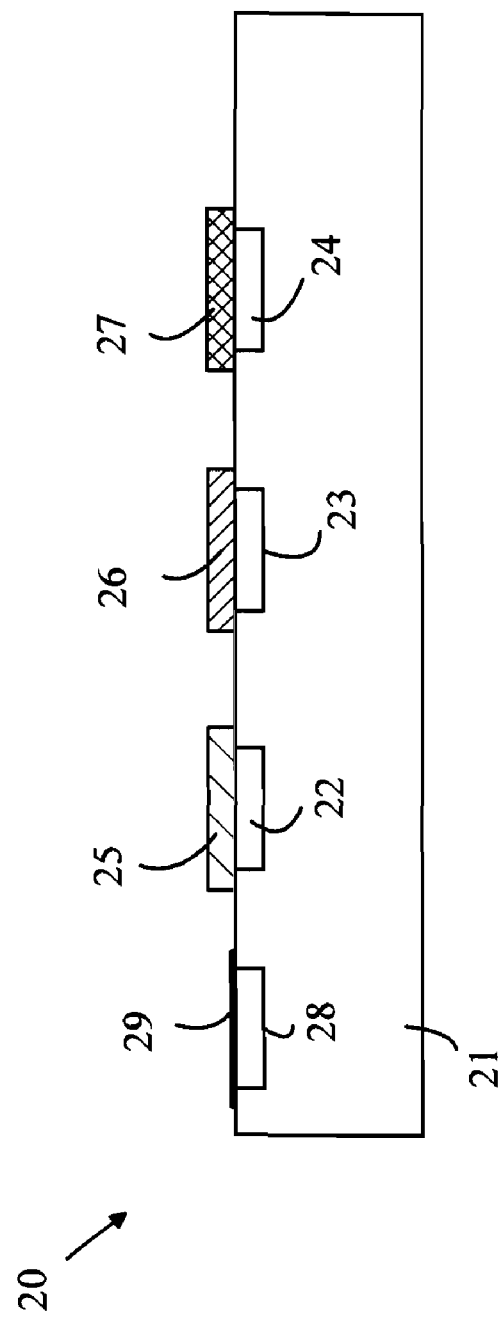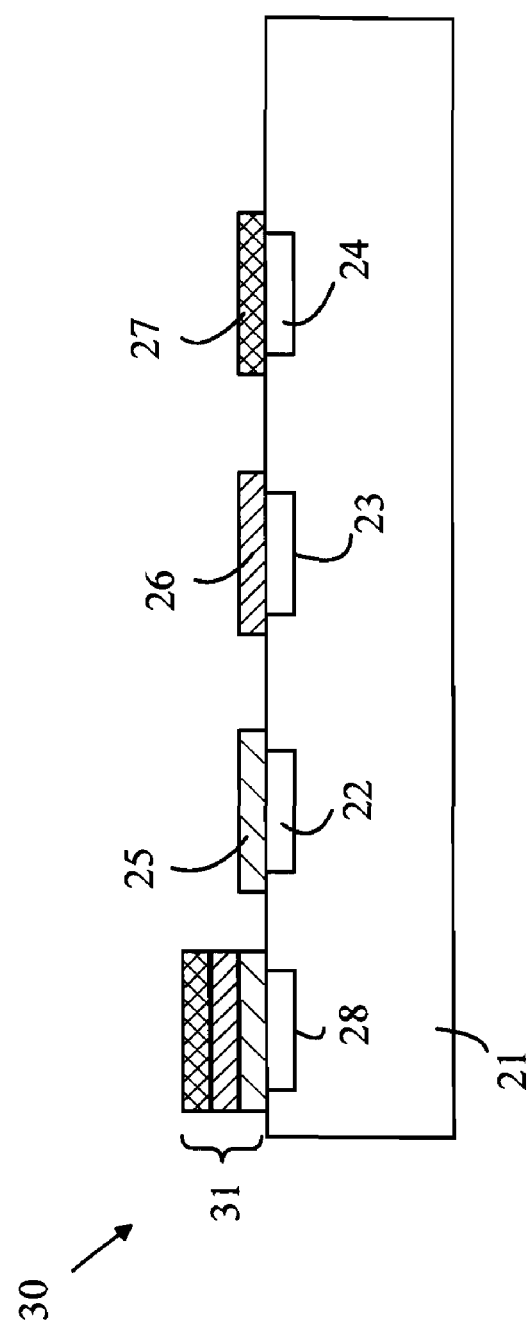

PHOTODETECTOR HAVING DARK CURRENT CORRECTION

BACKGROUND OF THE INVENTION

Inexpensive photodetectors that measure the intensity of light in a number of wavelength bands are required in a number of devices. For example, light sources that utilize red, blue, and green LEDs to generate light that is perceived as being a particular color often utilize photodetectors in a servo loop that maintains the output of the LEDs at predetermined levels to compensate for aging. The photodetectors are used to measure the output of each LED. A controller adjusts the average current to each LED such that the measured outputs are maintained at target values determined by the perceived color of light that is to be generated.

In one commonly used type of photodetector, the photodetector utilizes photodiodes that are covered by pigment filters that limit the response of each of the photodiodes to light in a corresponding band of wavelengths. The signals from the various photodiodes are processed to provide signals that represent the output of each of the LEDs. The signal from each photodiode is determined by the incident light, the band-pass filter characteristics of the pigment and various background signals that are present independent of the intensity level of the light reaching the photodiode. The light-independent signals are often referred to as the "dark current". The errors generated by the dark current can be significant in a number of applications; hence, schemes for correcting for the dark current have been developed. In addition, removing the contributions to the final signals that result from the dark current improves the dynamic range of the photodetector, and hence, the photodetector can be used to control the LEDs over a larger range of light intensities.

In one dark current correction scheme, the errors generated by the dark current are removed by measuring the output of the photodiode when no light is present and then subtracting the measured signal value from the signals generated by the photodiode in the presence of light. In this arrangement, the photodiodes are identical in structure and differ only in the type of pigment filter that overlies each photodiode. An additional photodiode that is covered by an opaque layer that blocks all light is included in the photodetector. The signal from this photodiode is then subtracted from that generated by the photodiodes that are covered with the various pigment filters. This scheme, however, significantly increases the cost of the photodetectors, since additional masking steps are needed to provide the opaque layer over the additional photodiode.

SUMMARY OF THE INVENTION

The present invention includes a substrate having first, second, and third photodiodes and first and second pigment filter layers. The first, second, and third photodiodes generate first, second, and third photodiode output signals, respectively, each photodiode output signal being indicative of a light intensity incident on that photodiode and a dark current that is independent of the light intensity. The first pigment filter layer overlies the first photodiode but not the second photodiode, and is transparent to light in a first band of wavelengths and opaque to light in a second band of wavelengths. The second pigment filter layer overlies the second photodiode, but not the first photodiode. The second pigment filter layer is transparent to light in the second band of wavelengths and opaque to light in the first band of wavelengths. A layer that includes the first and second pigment filter layers overlies the third photodiode. An output circuit combines the first and third photodiode output signals to provide a first corrected output signal and the second and third photodiode output signals to provide a second corrected output signal. In one aspect of the invention, the first, second, and third photodiodes have the same dark current.

BRIEF DESCRIPTION OF THE DRAWINGS

FIG. 1 is a cross-sectional view of a prior art photodetector that utilizes pigment filters.

FIG. 2 is a cross-sectional view of a photodetector according to one embodiment of the present invention.

DETAILED DESCRIPTION OF THE PREFERRED EMBODIMENTS OF THE INVENTION

Figure 3:
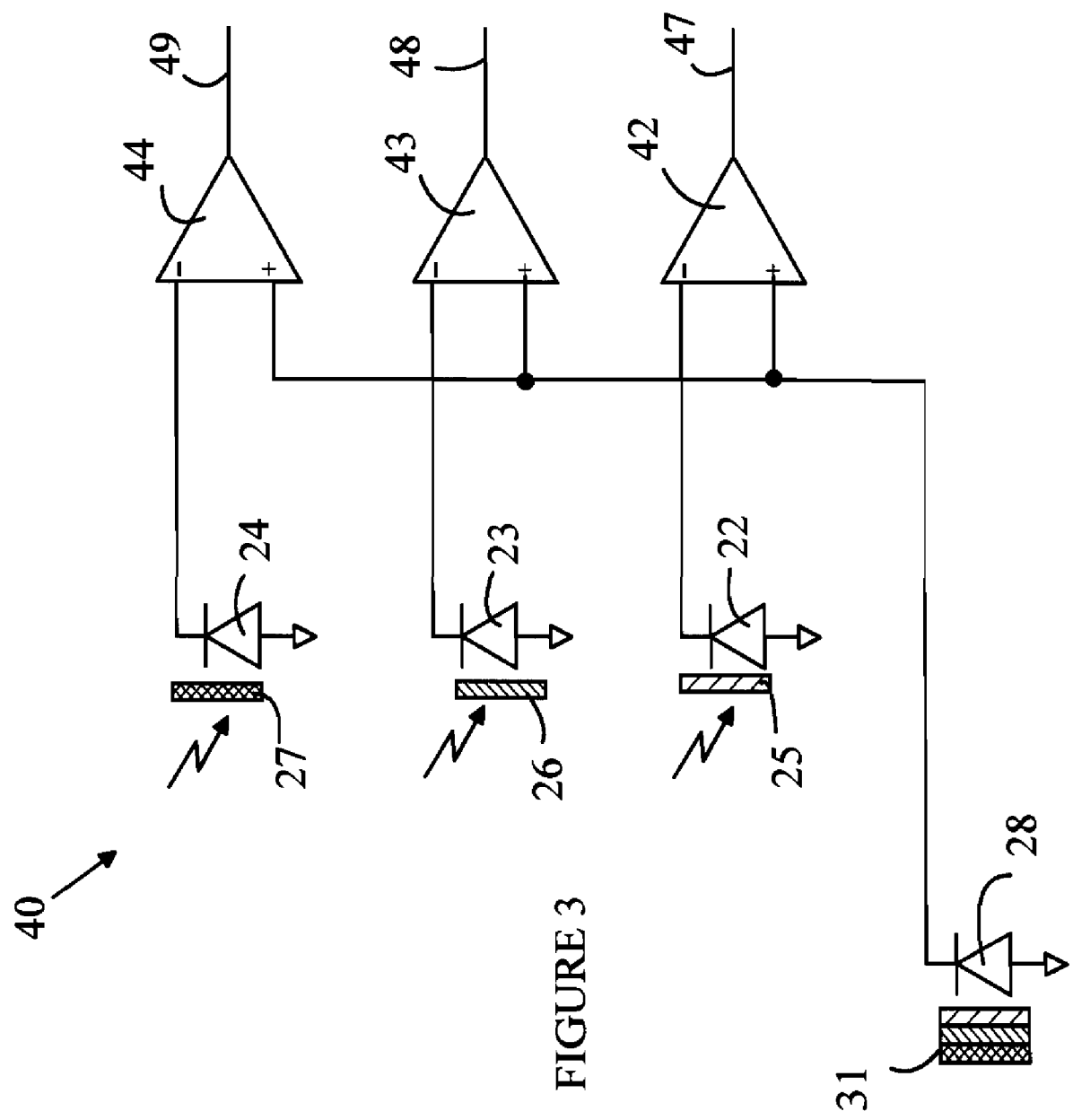
FIG. 3 is a schematic drawing of a photodiode according to another embodiment of the present invention.

The manner in which the present invention provides its advantages can be more easily understood with reference to FIG. 1, which is a cross-sectional view of a prior art photodetector that utilizes pigment filters. Photodetector 20 is typically constructed from a die 21 having 4 photodiodes fabricated thereon. Photodiodes 22-24 are used to measure the intensity of light in three wavelength bands that are determined by pigment filters 25-27, respectively. Photodiode 28 is covered by an opaque layer 29 and is utilized to measure the dark current. The pigment filters are applied by photolithographic steps that require a number of masking and deposition steps. A similar photolithographic step is needed for applying layer 29.

Refer now to FIG. 2, which is a cross-sectional view of a photodetector according to one embodiment of the present invention. In photodiode 30, the opaque layer that covered dark current detector 28 is replaced by a stack 31 of pigment filters that utilize the same pigments as filters 25-27. The signal from photodiode 28 provides the dark current signal that was previously measured using opaque layer 29. Hence, by subtracting the signal from photodiode 28 from the signals generated by each of the other photodiodes, the photodiode signals can be corrected for dark current.

Refer now to FIG. 3, which is a schematic drawing of a photodiode according to another embodiment of the present invention. Photodiode 40 utilizes the chip shown in FIG. 2 to generate 3 corrected photodiode signals 47-49. The corrected signals are generated by subtracting the output of photodiode 28 from each of the outputs of photodiodes 22-24 using subtraction circuits 42-44.

The above-described embodiments of the present invention assume that the incident light is restricted to light in the visual portion of the optical spectrum. In particular, the above-described embodiments assume that the incident light is devoid of light in the infrared portion of the spectrum. Most commonly used photodiodes are sensitive to light in the infrared portion of the spectrum. In addition, the pigment filters that are typically used, transmit light in the infrared portion of the spectrum in addition to the light in the band of wavelengths of interest.

If each of the pigment filters is essentially transparent in the infrared region of the spectrum, the arrangement shown in FIG. 3 will also correct for any infrared radiation in the incident light. In this case, the signal from each of the photodetectors will also include a component that has a magnitude equal to that of the infrared radiation. Since all of the photodiodes are assumed to be identical, the subtraction of the signal from the photodiode having the stacked pigment filters will also correct the signals for the infrared component in the incident light. If pigment filters partially attenuate the infrared light, then the correction provided by the embodiment shown in FIG. 3 will only partially correct for the infrared component in the incident light. However, the correction will still be better than that provided by utilizing an opaque layer over the photodiode used to measure the dark current.

It should be noted that the dark current correcting filter utilized in the present invention does not require any new fabrication steps beyond those used to deposit the other bandpass pigment filters. For example, in a lithographic deposition scheme, each photodiode is provided with a pigment filter by masking the other photodiodes and then depositing the pigment over the photodiode in question. The mask is then removed and a new mask that covers all but the next photodiode is introduced. A layer of pigment is then deposited over the unmasked layers. The process is repeated until each photodiode is covered with the pigment corresponding to that photodiode. The dark current filter of the present invention can be constructed at the same time as the bandpass filters by leaving the area over the photodiode in question unmasked during each of the deposition steps used to deposit the other pigment layers. Hence, no new masks and deposition steps need be used.

In one embodiment of the present invention, the pigments are the red, blue, and green pigments that are normally utilized to construct photodetectors. Such filters are used in imaging arrays that are used in digital cameras, and hence, will not be discussed in detail here.

The above-described embodiments of the present invention utilize a pigment stack having all of the layers that are applied to the other photodiodes to construct the opaque layer that is used to shield the photodiode used to generate the dark current signal. However, less than the entire set of pigment filters could be utilized. For example, the combination of a blue and red bandpass filter could, in some cases, be sufficiently opaque to provide the required shielding of the underlying photodetector. This more limited stack of filters is useful in cases in which the thicker full pigment filter stack cannot be utilized due to problems maintaining the thicker stack. For example, the thicker stack of filters could be subject to detachment during temperature cycling.

It should be noted that such a limited stack of filter layers can still be provided without any new masking and/or deposition steps. For example, consider the case in which the green pigment filter is to be omitted from the filter stack. The deposition of the green pigment includes three steps. The first step deposits a patterned mask over the areas that are not to be covered by the green pigment in the final photodetector. In the second step, the pigment is deposited, and finally, the mask is removed in the third step. If the green pigment is to be eliminated from the stack, the patterned mask is set such that the mask extends over the area above the dark current photodiode.

Figure 4:
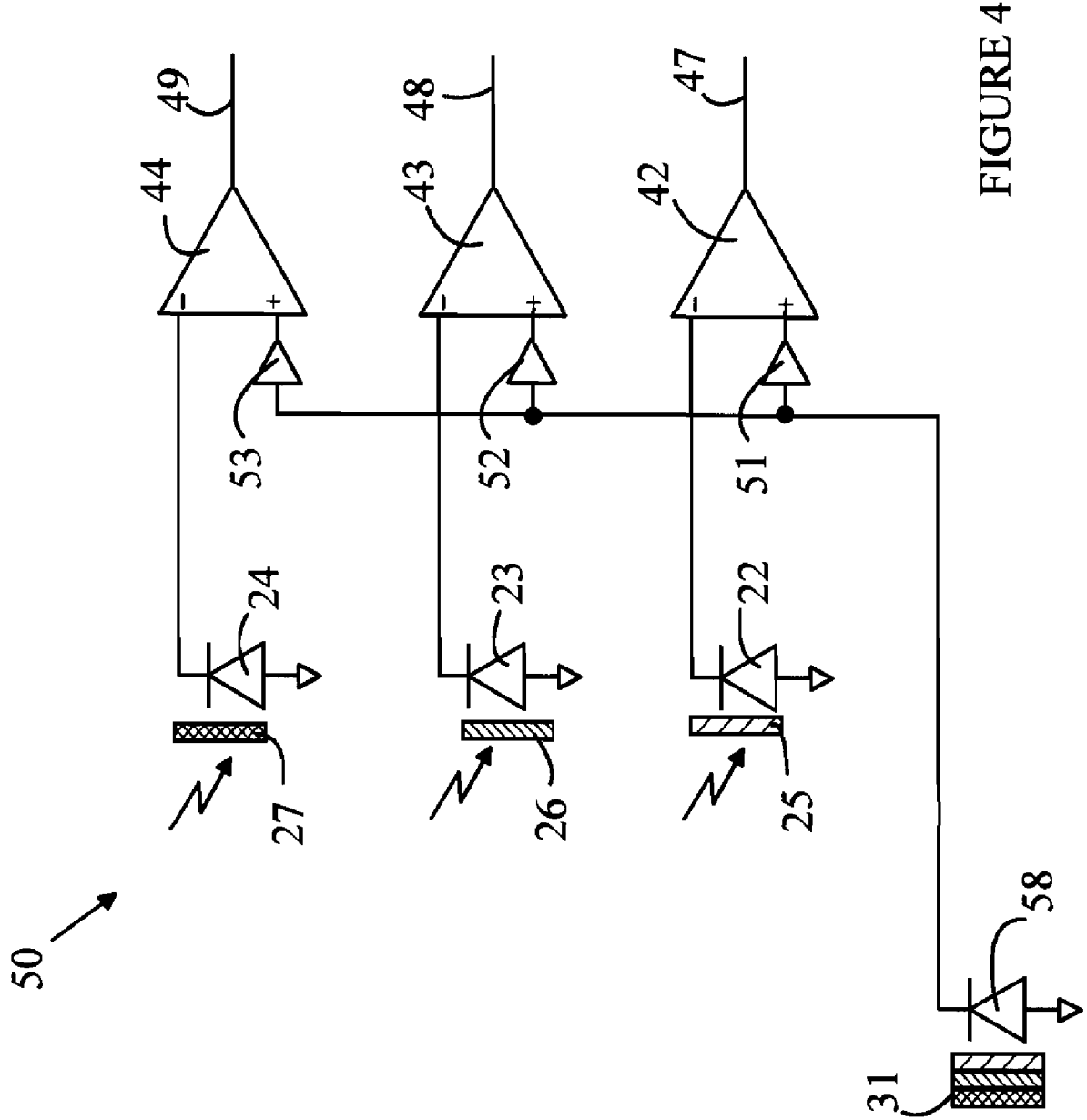
FIG. 4 is a schematic drawing of a photodiode according to another embodiment of the present invention.

The above-described embodiments of the present invention utilize photodiodes that are identical in structure for both the dark current sensing photodiode and the band pass sensing photodiodes. However, embodiments in which the photodiodes have different dimensions could also be utilized. For example, the photodiodes could have areas that are integer multiples of the area of one of the photodiodes. In such cases, the ratio of the dark current in the dark current sensing photodiode to the dark current in the band pass sensing photodiodes would need to be known. The output from the dark current sensing photodiode could then be scaled with an appropriate amplifier or attenuator to account for the different structures. Refer now to FIG. 4, which is a schematic drawing of a photodiode according to another embodiment of the present invention. Photodiode 50 differs from photodiode 40 discussed above in that photodiode 28 is replaced by photodiode 58 that has a different structure than the remaining photodiodes. In this case, photodiode 58 has a dark current that is different from the dark currents of the remaining photodiodes; however, the dark current of photodiode 58 has a fixed value, and hence, the dark current from photodiode 58 can still be utilized to correct for the dark current of the other photodiodes by utilizing an appropriate amplifier or attenuator to scale the output of photodiode 58 before subtracting that output from the output of each of the other photodiodes. This scaling operation is performed by amplifiers 51-53. It is to be understood that amplifiers 51-53 could have gains that are less than 1, i.e., amplifiers 51-53 could be attenuators.

The above discussion refers to the pigment layers as being "transparent" and "opaque" to light in various bands of wavelengths. Ideally, a transparent layer has 100% transmission for light in the relevant wavelength band and the opaque layer has 0% transmission for light in the relevant wavelength band. However, it will be appreciated that pigments that are only partially transparent or partially opaque could be utilized and still provide a photodetector that is superior to the prior art photodetectors in particular applications. Hence, the term "transparent layer" is defined to include layers that have sufficient transmission to allow the photodiode under the layer to measure light in the relevant wavelength band in the presence of light in a band in which the layer is said to be opaque even though the layer has some transmission in the band to which it is said to be opaque. In particular, the term "transparent layer" includes layers that have transmissions greater than 60 percent. Similarly, the term "opaque layer" is defined to include layers that have transmissions less than 30 percent.

Various modifications to the present invention will become apparent to those skilled in the art from the foregoing description and accompanying drawings. Accordingly, the present invention is to be limited solely by the scope of the following claims.

What is claimed is:

1. A photodetector comprising:

a substrate having first, second, and third photodiodes that generate first, second, and third photodiode output signals, respectively, each photodiode output signal being indicative of a light intensity incident on that photodiode;

a first pigment filter layer overlying said first photodiode but not said second photodiode, said first pigment filter layer being transparent to light in a first band of wavelengths and opaque to light in a second band of wavelengths;

a second pigment filter layer overlying said second photodiode, but not said first photodiode, said second pigment filter layer being transparent to light in said second band of wavelengths and opaque to light in said first band of wavelengths;

a layer comprising said first and second pigment filter layers overlying said third photodiode; and an output circuit that combines said first and third photodiode output signals to provide a first corrected output signal and that combines said second and third photodiode output signals to provide a second corrected output signal.

2. The photodetector of claim 1 wherein said output circuit subtracts a signal that is a multiple of said third photodiode output signal from said first and second photodiode output signals.

3. The photodetector of claim 1 wherein said first, second, and third photodiodes have areas that are integer multiples of the area of one of said photodiodes.

4. The photodetector of claim 1 further comprising a fourth photodiode and a third pigment filter layer overlying said fourth photodiode but not said first and second photodiodes, said fourth photodiode generating a fourth photodiode output signal indicative of a light intensity incident on said fourth photodiode and a dark current that is independent of that light intensity, wherein said output circuit further combines said third and fourth photodiode output signals to provide a third corrected output signal.

5. The photodetector of claim 4 wherein said third corrected output signal is corrected for said dark current.

6. The photodetector of claim 4 wherein said third pigment layer also overlies said third photodiode.

7. The photodetector of claim 1 wherein each of said photodiodes generates a dark current in the absence of light being received by said photodiodes and wherein said first and second output signals depend less on said dark current than said first and second photodiode output signals.

* * * * *